United States Patent
Harada et al.

(12) 
(10) Patent No.: US 6,674,836 B2
(45) Date of Patent: Jan. 6, 2004

(54) X-RAY COMPUTER TOMOGRAPHY APPARATUS

(75) Inventors: Toyoshige Harada, Shioya-gun (JP); Sanae Harada, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 429 days.

(21) Appl. No.: 09/760,780

(22) Filed: Jan. 17, 2001

(65) Prior Publication Data

US 2001/0008552 A1 Jul. 19, 2001

(30) Foreign Application Priority Data

Jan. 17, 2000 (JP) ........................... 2000-007815

(51) Int. Cl.⁷ ................................. H05G 1/14
(52) U.S. Cl. ........................................ 378/107
(58) Field of Search .......................... 378/4, 10, 107, 378/101, 111, 112

(56) References Cited

U.S. PATENT DOCUMENTS 4,912,735 A 3/1990 Beer ........................... 378/15
5,105,351 A 4/1992 Harada et al. .............. 378/101
5,272,612 A 12/1993 Harada et al. .............. 378/101

FOREIGN PATENT DOCUMENTS

JP 7-204192 8/1995
JP 8-336521 12/1996

*Primary Examiner*—William Oen
(74) *Attorney, Agent, or Firm*—Oblon, Spivak, McClelland, Maier & Neustadt, P.C.

(57) ABSTRACT

An X-ray computer tomography apparatus comprises a high-voltage transformer which performs the increase and noncontacting transmission of the power simultaneously and outputs a desired high voltage for causing X rays to be generated at the rotatable gantry section. The high-voltage transformer is divided into a primary-side which is provided on the static gantry section and to which the output of a frequency converting circuit is supplied and a secondary-side which generates a high voltage. A capacitor is connected to a secondary coil of the high-voltage transformer, thereby forming a resonance circuit.

20 Claims, 6 Drawing Sheets

X-RAY COMPUTER TOMOGRAPHY APPARATUS

CROSS-REFERENCE TO RELATED APPLICATIONS

This application is based upon and claims the benefit of priority from the prior Japanese Patent Application No. 2000-007815, filed Jan. 17, 2000, the entire contents of which are incorporated herein by reference.

BACKGROUND OF THE INVENTION

This invention relates to an X-ray computer tomography apparatus, and more particularly to a thin-type X-ray computer tomography apparatus (hereinafter, referred to as an X-ray CT apparatus) provided with a small-sized high-voltage transformer capable of supplying power and stepping up the voltage by itself in a noncontacting manner.

In the field of X-ray CT apparatuses, high-speed tomographic techniques for turning the rotatable gantry section with respect to the static gantry section at high speed are being developed rapidly. With the high-speed tomographic techniques, not only a larger amount of image information can be obtained in a short time but also the time during which the subject is tied down. Thus, the techniques are very effective in a group medical examination as well as an ordinary physical examination. In recent years, a high-speed rotation of about 0.5 second has already been put to practical use and further an ultrahigh-speed rotation of less than 0.3 second is gradually gaining practicality.

Because of the problem of centrifugal force acting on the rotatable gantry section by high-speed rotation, the gantry of the X-ray CT apparatus have been required to be made smaller in size, particularly thinner along the axis of the body of the subject. Although various measures have been taken to improve the method of arranging the units in the rotatable gantry section, it is necessary to make each unit as small as possible to reduce the size of the rotatable gantry section itself. In the X-ray CT apparatus, the top on which the subject has been laid is inserted into a cylindrical space formed within the rotatable gantry section and then pictures are taken. In such an X-ray CT apparatus, it is necessary to improve the accessibility of the subject as in the magnetic resonance imaging apparatus. An improvement in the accessibility enables various medical procedures when the subject is inserted into the apparatus. Moreover, the subject has a less feeling of confinement in the cylindrical space.

The power supply from the static gantry section to the rotatable gantry section is carried out in a contacting manner or a noncontacting manner. One example of supplying power in a contacting manner is achieved by using a slip ring mechanism. As is well known, the slip ring mechanism has a brush provided on the rotatable gantry section and causes the brush to come into contact with the slip ring provided on the static gantry section, thereby supplying power from the static gantry section to the rotatable gantry section. The slip ring mechanism is considered to be unsuitable for high-speed rotation, because the friction between the brush and the slip ring produces heat and abrasion powder. In addition, since there is a possibility of electric discharges, the slip ring is regarded as unsuitable for power transmission of such a high voltage, for example, 10 kV or more as is applied across both ends of an X-ray tube. Under these conditions, several concepts of X-ray CT apparatuses that supply power from the static gantry section to the rotatable gantry section in a noncontacting manner have been proposed.

One known noncontacting-type X-ray CT apparatus is disclosed in U.S. Pat. No. 4,912,735. This X-ray CT apparatus supplies power in a noncontacting manner by electromagnetic induction.

FIG. 11 is a schematic circuit diagram of a conventional X-ray CT apparatus that supplies power from the static gantry section to the rotatable gantry section. FIG. 12 shows the location of the individual component parts. In FIG. 12, an AC/DC converter 14b is connected to an alternating-current (a.c.) power source 11 provided on the side face of the lower part of the inside of the static gantry section 111. The output terminal of the AC/DC converter 14b is connected to an inverter 15. The output of the inverter 15 is connected to the primary coil 116 of the static gantry section 111. The primary coil 116 is wound around the cylindrical static gantry section 111 in such a manner that it surrounds the outer surface of the static gantry section 111. The rotatable gantry section 112 has a cylindrical shape as the static gantry section 111 does and is provided on the static gantry section 111 on the same central axis of the cylinder in such a manner that it can rotate. On the rotatable gantry section 112, a secondary coil 119 is provided in a position facing the primary coil 116 of the static gantry section 111. Like the primary coil 116, the secondary coil 119 is wound around the rotatable gantry section 112 in such a manner that it surrounds the outer surface of the rotatable gantry section 112. A high-voltage transformer 113 is connected to the secondary coil 119. A rectifier 20 is connected to the output terminal of the high-voltage transformer 113. An X-ray tube 21 is connected to the output terminal of the rectifier 20. A magnetic field generated at the primary coil 116 induces power at the secondary 119. The electromagnetic induction enables power to be supplied from the static gantry section 111 to the rotatable gantry section 112.

The conventional X-ray CT apparatus with the above configuration that supplies power in a noncontacting manner has the following problem.

As compared with an ordinary transformer where the cores are integrally formed, the leakage inductance between the cores of the separate primary coil 116 and secondary coil 119 is greater, impeding a high-frequency operation, which makes it difficult to miniaturize the unit. The miniaturization is possible only when the operation of the unit is carried out at higher speed. For this reason, in general, to reduce the leakage inductance, the primary coil 116 is arranged as close to the secondary coil 119 as possible or the coil windings are wound even in the grooves of the cores, thereby improving the degree of coupling. In such a manner of improving the degree of coupling, there arises a problem that realizing the high frequency operation by overcoming the leakage inductance between the separated cores is limited. Moreover, it makes high-voltage insulation difficult from the viewpoint of manufacturing techniques. Thus, to obtain a high voltage of about 75 kV to 150 kV on the secondary side, it is necessary to provide an additional high-voltage transformer 113. This puts significant restriction on the rotatable gantry section being made smaller and thinner. In the X-ray CT apparatus, the primary coil 116 is wound around the cylindrical static gantry section 111 in such a manner that it surrounds the outer surface of the static gantry section 111 and the secondary coil 119 is wound around the rotatable gantry section 112 in such a manner that it surrounds the outer surface of the rotatable gantry section 112, with the result that the distance between the windings facing each other is relatively long. This makes the parasitic capacitance large, making a high-frequency operation difficult, which is one of the causes of the difficulty in making the unit smaller and thinner.

Another known noncontacting X-ray CT apparatus is disclosed in Jpn. Pat. Appln. KOKAI Publication No. 7-204192 and Jpn. Pat. Appln. KOKAI Publication No. 8-336521. Each of these conventional X-ray CT apparatuses has the following configuration.

Each of the X-ray CT apparatuses comprises electromagnetic induction transmission means including a first winding provided on the fixed frame of a scanner and a second winding provided on the rotary section of the scanner in such a manner that it faces the first winding, and a high-voltage generator connected to the electromagnetic induction transmission means. Each of the X-ray CT apparatuses supplies specific power in a noncontacting manner by electromagnetic induction.

Each of these conventional X-ray CT apparatuses is provided with an additional high-voltage transformer to obtain a high voltage, because of the problem of the leakage inductance, as explained in the X-ray CT apparatus disclosed in U.S. Pat. No. 4,912,735. This is a serious hindrance in making the rotatable gantry section smaller and thinner.

Each of U.S. Pat. No. 5,105,351 and U.S. Pat. No. 5,272,612, which are assigned to the same assignee as the present invention, discloses a device for applying a high voltage to an X-ray tube. Each of these two devices includes a plurality of high-voltage transformers, taking the size reduction of transformers into account. However, there is no reference to noncontacting power supply by electromagnetic induction or a concrete application of the inventions to an X-ray CT apparatus.

BRIEF SUMMARY OF THE INVENTION

The object of the present invention is to provide a thin-type and small-sized X-ray computer tomography apparatus.

According to the present invention, there is provided an X-ray computer tomography apparatus comprising: a static gantry section; a rotatable gantry section which is provided on the static gantry section in a rotatable manner and has an X-ray tube for generating X rays; a frequency converting circuit which is connected to an alternating-current power source and converts the output voltage from the alternating-current power source into a desired high-frequency voltage; a high-voltage transformer which transmits the output of the frequency converting circuit from the static gantry section to the rotatable gantry section and steps up the output to a desired high voltage; and a rectifier circuit which converts the alternating-current voltage outputted from the high-voltage transformer into a direct-current voltage and supplies the direct-current voltage to the X-ray tube, wherein the high-voltage transformer including: a primary-side which is provided on the static gantry section and to which the output of the frequency converting circuit is supplied, and a resonance circuit with a capacitor connected to a winding of a secondary-side, which is provided on the rotatable gantry section and generates the high voltage.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, referring to the accompanying drawings, embodiments of the present invention will be explained.

Figure 1:
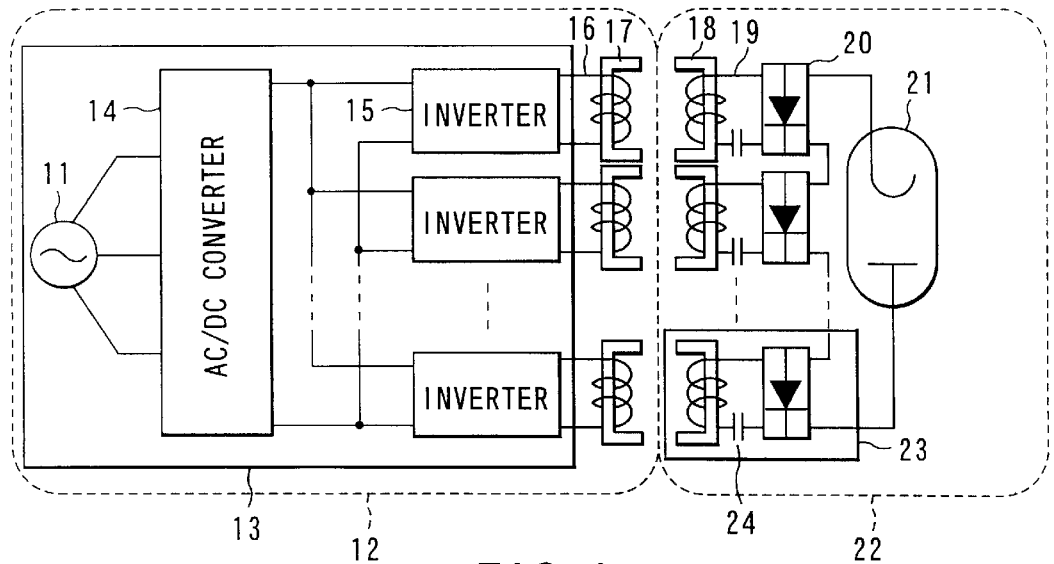
FIG. 1 shows the configuration of a circuit for supplying power from the static gantry section to the rotatable gantry section in an X-ray CT apparatus according to a first embodiment of the present invention.
Figure 2:
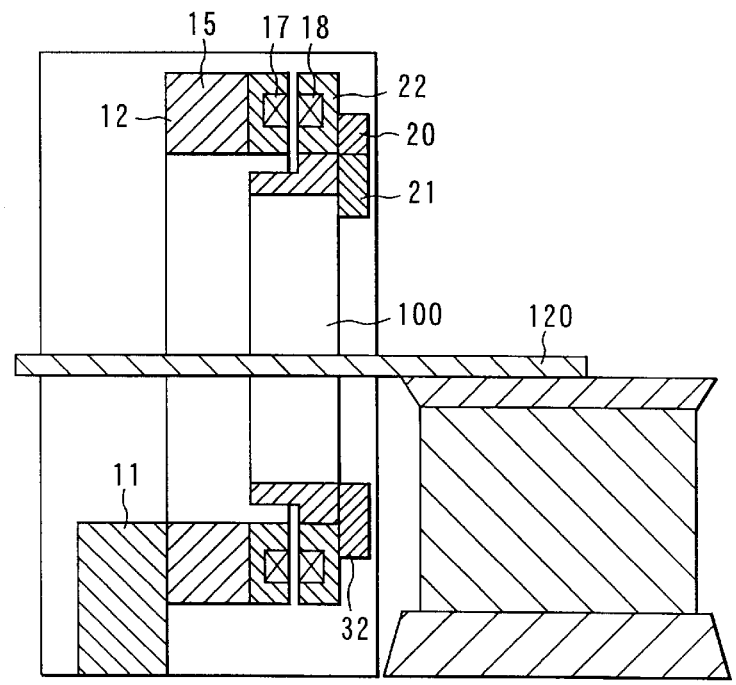
FIG. 2 is a sectional view showing the location of the individual parts inside the static gantry section and rotatable gantry section.

FIG. 1 shows the configuration of a circuit for supplying power from the static gantry section to the rotatable gantry section in an X-ray CT apparatus according to a first embodiment of the present invention. FIG. 2 is a sectional view showing the location of the individual parts inside the static gantry section and rotatable gantry section.

Figure 11:
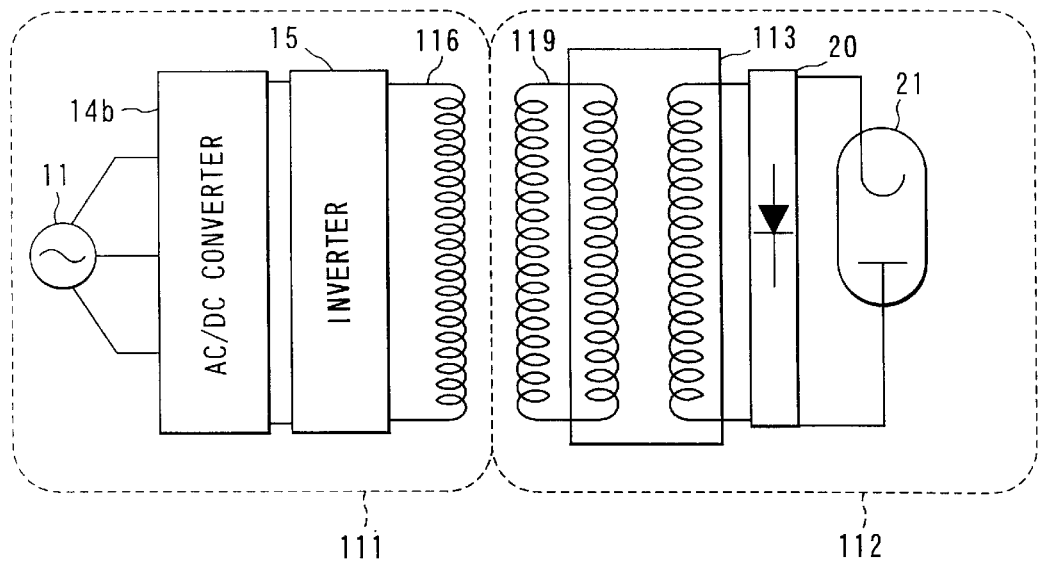
FIG. 11 shows the configuration of a circuit for supplying power from the static gantry section to the rotatable gantry section in a conventional X-ray CT apparatus.

As shown in FIG. 11 the X-ray CT apparatus of the first embodiment is composed of a static gantry section 12 and a rotatable gantry section 22 roughly divided as shown by broken lines. The static gantry section 12 includes an alternating-current (a.c.) power generator section 13 composed of an a.c. power source 11, an AC/DC converter 14, and an inverter 15 and a transformer fixing section 51. The rotatable gantry section 22 includes a transformer rotating section 52, a rectifier 20, and an X-ray tube 21.

The transformer fixing section 51 provided on the static gantry section 12 and the transformer rotating section 52 provided on the rotatable gantry section 22 constitute a separate-type high-voltage transformer 50. The transformer fixing section 51 includes a primary coil 16 and a primary side core 17. The transformer rotating section 52 includes a secondary coil 19 and a secondary side core 18. The primary side core 17 is not formed integrally with the secondary side core 18. The arrangement of the primary side core 17 and secondary side core 18 will be explained in a second embodiment of the present invention.

The AC/DC converter 14 is connected to the output terminal of the alternating-current (a.c.) power source 11 serving as an input power source. A plurality of inverters 15 are connected in parallel with the output terminal of the AC/DC converter 14. The output terminal of each of the inverters 15 is connected to the primary coil 16 of the transformer fixing section 16. The AC/DC converter 14 converts the a.c. voltage from the a.c. power source 11 into a direct-current (d.c.) voltage. The d.c. voltage is then supplied to the inverter 15, which converts the d.c. voltage into a high-frequency a.c. voltage.

The reason why a plurality of inverters 15 are used in FIG. 1 is to prevent the whole of the X-ray CT apparatus from stopping the operation if one of the inverters 15 fails. By selecting the troubled inverter 15 and stopping it, the power can be controlled roughly. For the convenience of design, only one inverter 15 may be provided. The high frequency a.c. power generator 13 may have another configuration, as long as it generates power of desired frequency, for example, about 100 kHz.

The output of the high frequency a.c. power generator 13 is connected to the primary coil 16. When a plurality of inverters 15 are used, such as this embodiment, the output of each of the plurality of converters 15 is provided to the respective primary coils 16. Alternatively, if only one inverter 15 is used, the output of the inverter 15 is parallelly connected to a plurality of primary coils 16.

As shown in FIG. 2, the static gantry section 12 is mounted on a base 60. Near the static gantry section 12, the a.c. power source 11 is provided. The static gantry section 12 has an opening 101. Along to the cylindrical direction on outside of the opening 101, the inverter 15, primary coil 16, primary side core 17, and others are arranged. A doughnut-like disk rotatable gantry section 22 with an opening 100 in it is provided on the static gantry section 12 in such a manner that it can rotate continuously. The top 120 is inserted into the opening 101 of the static gantry section 12 and the opening 100 of the rotatable gantry section 22.

Outside the opening 100 of the rotatable gantry section 22, the secondary side core 18, secondary coil 19, rectifier 20, and others are arranged. The X-ray tube 21 and X-ray detector 32 are provided on the rotatable gantry section 22 in such a manner that they face each other with the opening 100 between them.

The primary coil 16 is wound around almost the central part of the primary side core 17. Two primary coils 16 may be wound around one primary coil 17.

The primary coil 16 and the primary side core 17 are arranged around the static gantry section 12 so that the magnetic flux generated at the primary side core 17 may be supplied to the rotatable gantry section 22.

The shape of the primary 17 is not limited to the squared-U shape. As long as the magnetic flux generated at the primary side core 17, together with the secondary side core 18 arranged so as to face the primary side core 17, can form a magnetic circuit, the primary side core may take another shape.

The squared-U-shaped secondary side core 18 facing the primary side core 17 is arranged around the ringed rotatable gantry section 22 placed so as to surround the top 120 of the couch, as is the primary side core 17.

In this case, too, the secondary side core 18 may take another shape, as long as it, together with the primary side core 17, can form a magnetic circuit.

The secondary coil 19 is wound around almost the central portion of the secondary side core 18.

As shown in FIG. 1, a capacitor 24 is connected in series with the secondary coil 19. The secondary capacitor 24 is designed to resonate with the inductance of the secondary coil 19. The inductance of the secondary coil 19 makes the impedance higher as the frequency increases, which is one of the factors that hinder the high-frequency operation most. When a suitable value of the secondary capacitor is selected, the secondary impedance can be adjusted by resonance, which enables a high-frequency operation.

Figure 12:
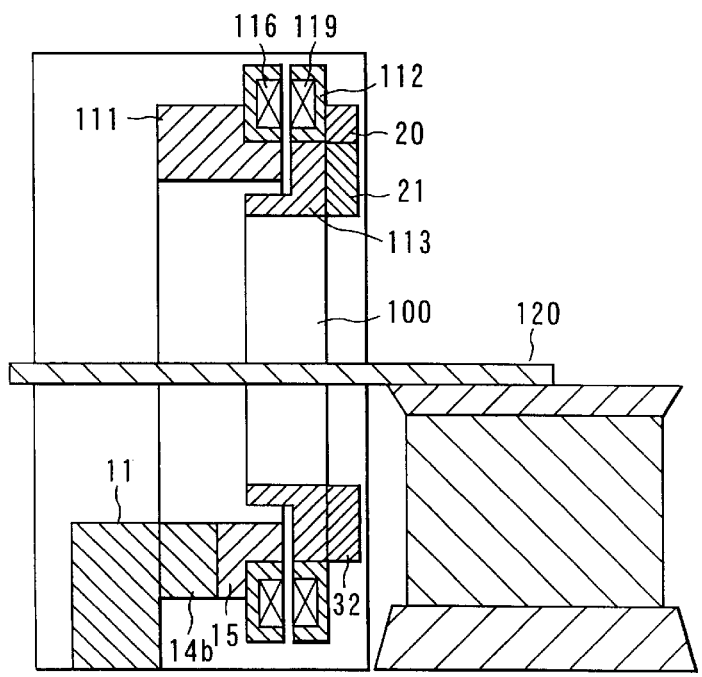
FIG. 12 is a sectional view showing the location of the individual parts inside the static gantry section and rotatable gantry section in the conventional X-ray CT apparatus.

In the conventional X-ray CT apparatus in each of FIG. 11 and FIG. 12, only one secondary coil 19 was used. Since the resonance voltage at the secondary coil 19 is overhigh than the necessary output voltage of 10 kV or higher, it is technically difficult to produce an insulting of the secondary coil 19. Furthermore, it is technically difficult to produce a capacitor capable of withstanding such a high voltage by itself. To overcome this drawback, the first embodiment uses a plurality of secondary coils 19, thereby lowering the voltage generated in each secondary coil 19. This makes it technically easy to realize an insulting of the secondary coil 19 or the capacitor 24.

The series circuit of the secondary coil 19 and capacitor 24 is connected to the rectifier 20.

Although the number of rectifiers 20 is the same as that of capacitors 24, either the number of rectifiers 20 or that of capacitors 24 may be larger than the other. The rectifiers 20 rectify high frequency a.c. power into d.c. power. The secondary side core 18, secondary coil 19, secondary capacitor 24, and rectifier 20 on the rotatable gantry section 22 constitute a high-voltage unit 23.

The one-side ends of the high-voltage unit 23 are connected in series and similarly its other-side ends are connected in series. The resulting one end and other end are connected to one end and the other end of the X-ray tube 21, respectively. The high-voltage unit 23, X-ray tube 21, and X-ray detector 32 are provided around the rotatable gantry section 22, taking weight balance into account. In the conventional example, when the rotatable gantry section was rotating, the weight of the rotatable gantry section was large and developed a great centrifugal force of, for example, about 13 G, which was a factor preventing a high-speed rotating operation.

In the first embodiment, however, the series resonance on the secondary side enables a high-frequency operation, for example, an operation at 100 kHz, which helps make the inverter 15, primary coil 16, primary side core 17, secondary coil 19, and secondary side core 18 smaller and lighter. The smaller, lighter secondary coil 19 and secondary side core 18 particularly decrease the weight and space of the rotatable gantry section 22 remarkably. Since the secondary coils 19 and the secondary side cores 18 are circularly and evenly arranged on the rotatable gantry section, the section excels at rotation balance.

Also, since the capacitor 24 is provided for resonance, and certain degree of the leakage inductance of the secondary coil 19 is used for the construction of the resonance circuit, there is no need to take into account the leakage inductance of the secondary coil 19 as inhibition factor.

Therefore, the secondary coil 19 can be wound around the secondary side core 18 with a sufficient insulting distance between them. As high a voltage as 150 kV can be generated, making it unnecessary to provide an additional high-voltage transformer for generating a high voltage on the rotatable gantry section 22, which enables the rotatable gantry section 22 to be made smaller and thinner remarkably.

Because the decreased number of component parts on the rotatable gantry section makes room for the space of the rotatable gantry section, it is possible to realize an X-ray CT apparatus with multiple tubes. Use of an X-ray CT apparatus with multiple tubes can improve time resolution of acquired image.

Hereinafter, various modifications of the circuit for supplying power from the static gantry section to the rotatable gantry section in the X-ray CT apparatus according to the first embodiment will be explained.

Figure 3:
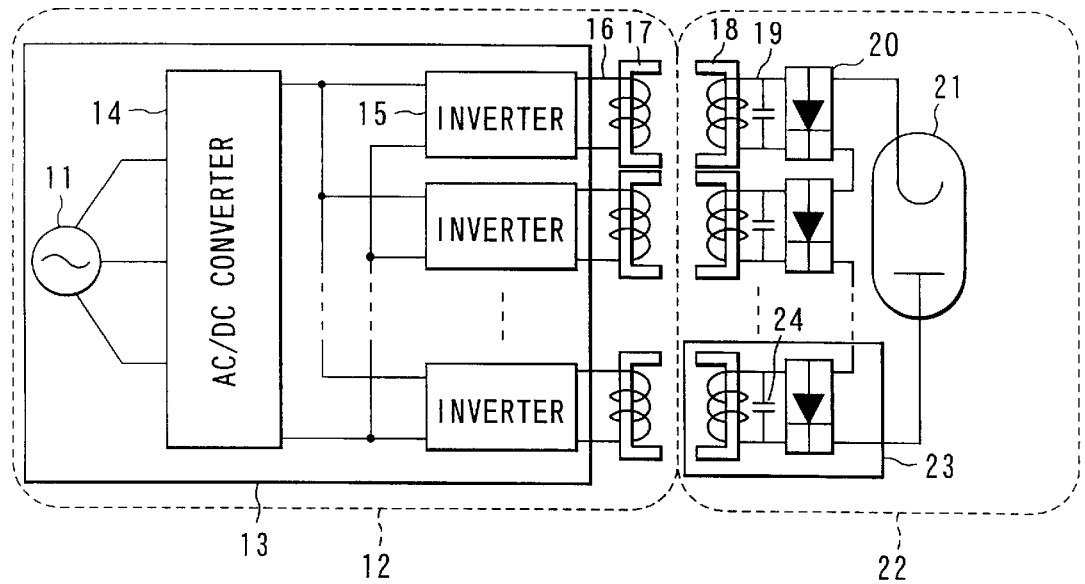
FIG. 3 shows a first modification of the circuit configuration of FIG. 1.

In a first modification of the first embodiment in FIG. 3, the capacitor 24 is connected in parallel with the secondary coil 19. The capacitor 24 resonates with the leakage inductance of the secondary coil 19.

Figure 4:
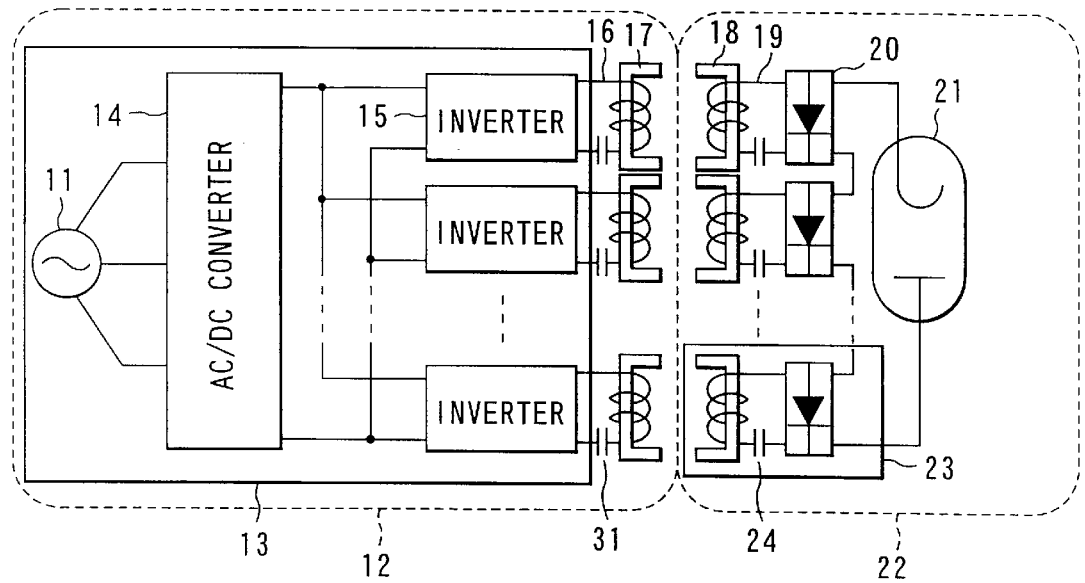
FIG. 4 shows a second modification of the circuit configuration of FIG. 1.
Figure 5:
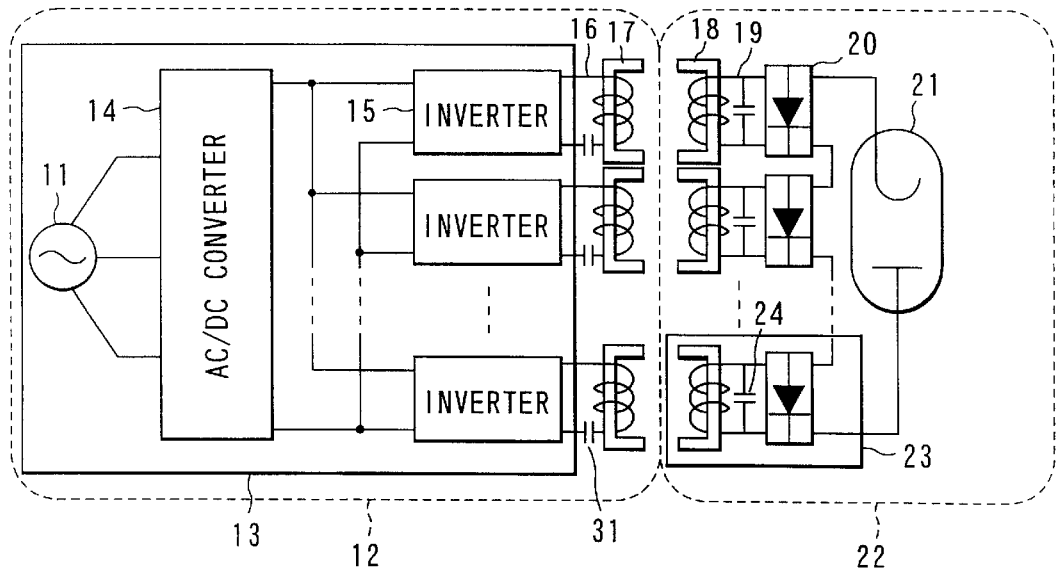
FIG. 5 shows a third modification of the circuit configuration of FIG. 1.
Figure 6:
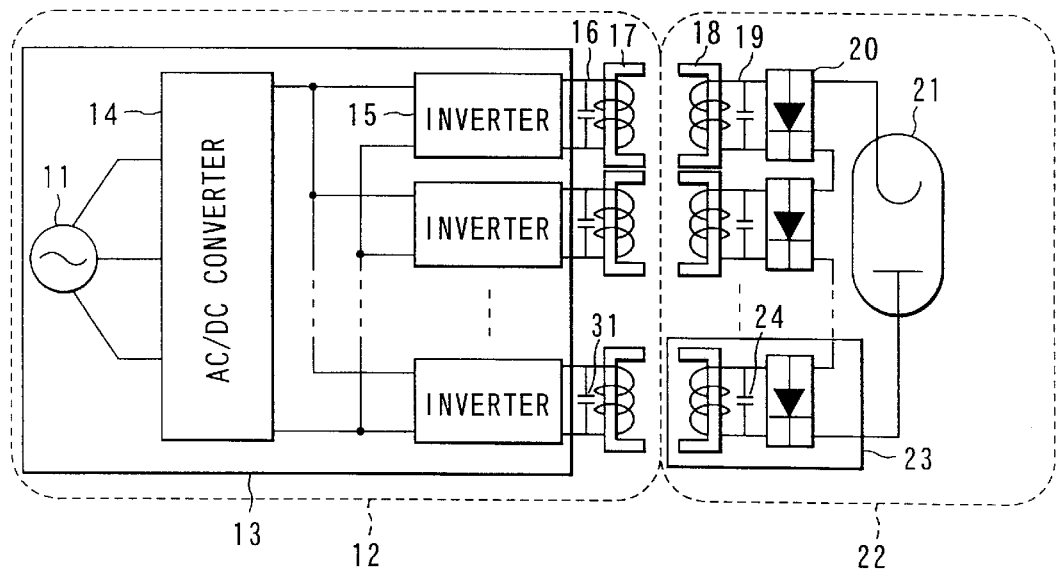
FIG. 6 shows a fourth modification of the circuit configuration of FIG. 1.

In a secondary modification of the first embodiment in FIG. 4, a capacitor 31 is inserted in series between the output of the high voltage a.c. power generator section 13 and the primary coil 16. In the second modification, the capacitor 24 is provided so as to resonate with the leakage inductance of the secondary coil 19 and the primary capacitor 31 is provided so as to resonate with the inductance of the primary coil 16. Even when resonance not only on the secondary side but also on the primary side make the operating frequency higher, the primary capacitor 31 and secondary capacitor 24 can be selected according to the resonance, which enables a high-frequency operation. That is, the primary-side leakage inductance can be used effectively in the secondary modification.

Figure 7:
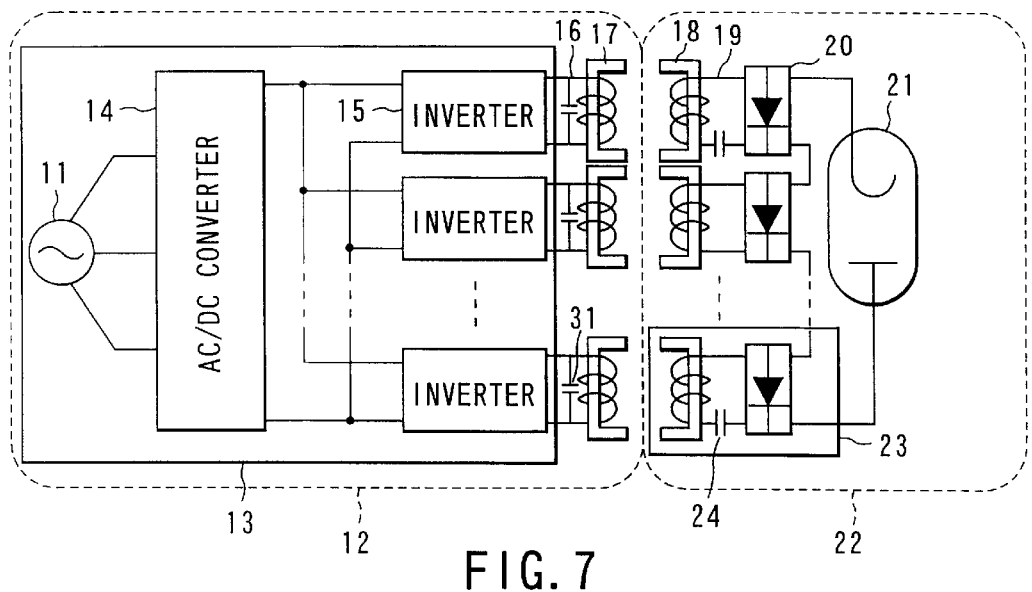
FIG. 7 shows a fifth modification of the circuit configuration of FIG. 1.

In a third modification of the first embodiment, the capacitor 31 is inserted in series between the output of the high frequency a.c. power generator 13 and the primary coil 16 and the capacitor 24 is connected in parallel with the secondary coil 19. In a fourth modification of the first embodiment, the capacitor 31 is inserted in parallel between the output of the high frequency a.c. power generator 13 and the primary coil 16 and the capacitor 24 is connected in parallel with the secondary coil 19. Furthermore, in a fifth modification of the first embodiment in FIG. 7, the capacitor 31 is inserted in parallel between the output of the high frequency a.c. power generator 13 and the primary coil 16.

Hereinafter, a second embodiment of the present invention will be explained.

Figure 8:
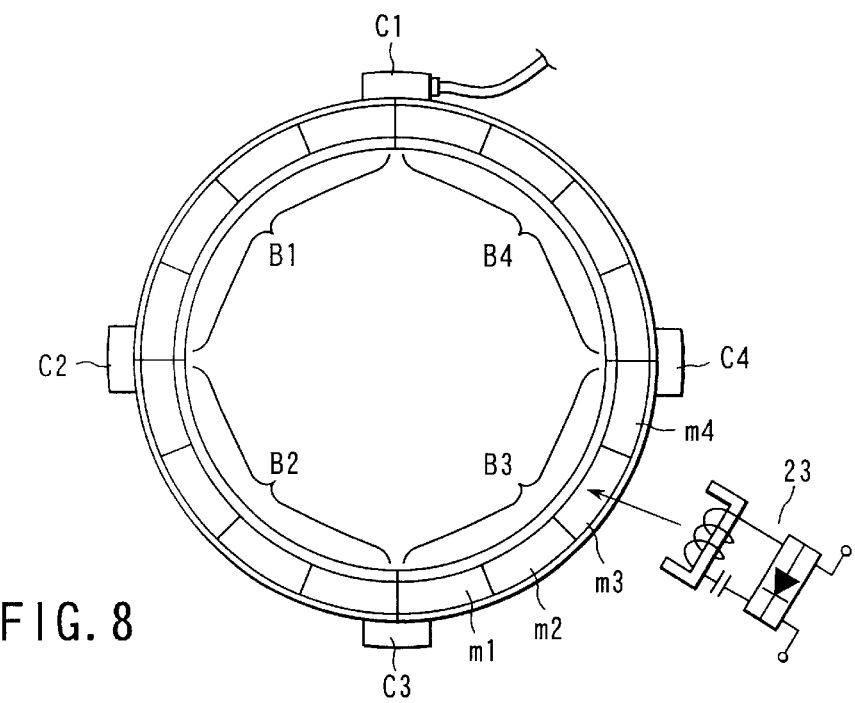
FIG. 8 shows a detailed configuration of the transformer rotating section in the rotatable gantry section in an X-ray CT apparatus according to a second embodiment of the present invention.
Figure 9:
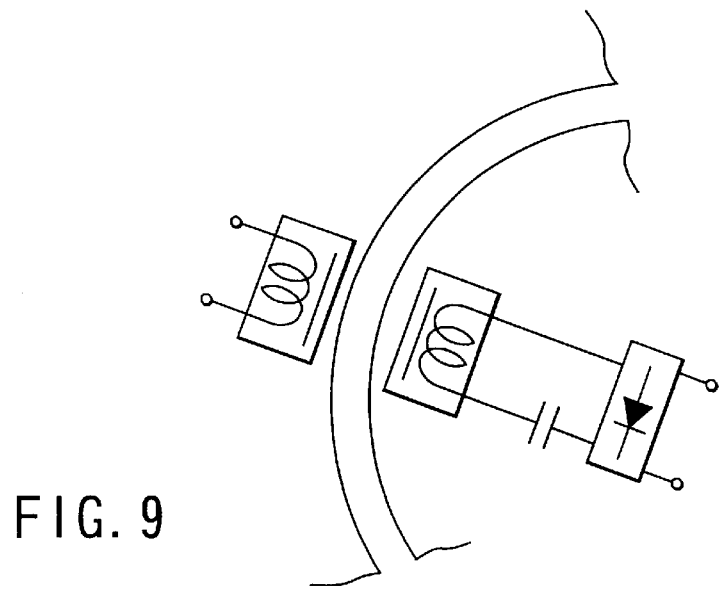
FIG. 9 shows the location of the transformer fixing section on the static gantry section and the transformer rotating section on the rotatable gantry section which face each other.
Figure 10:
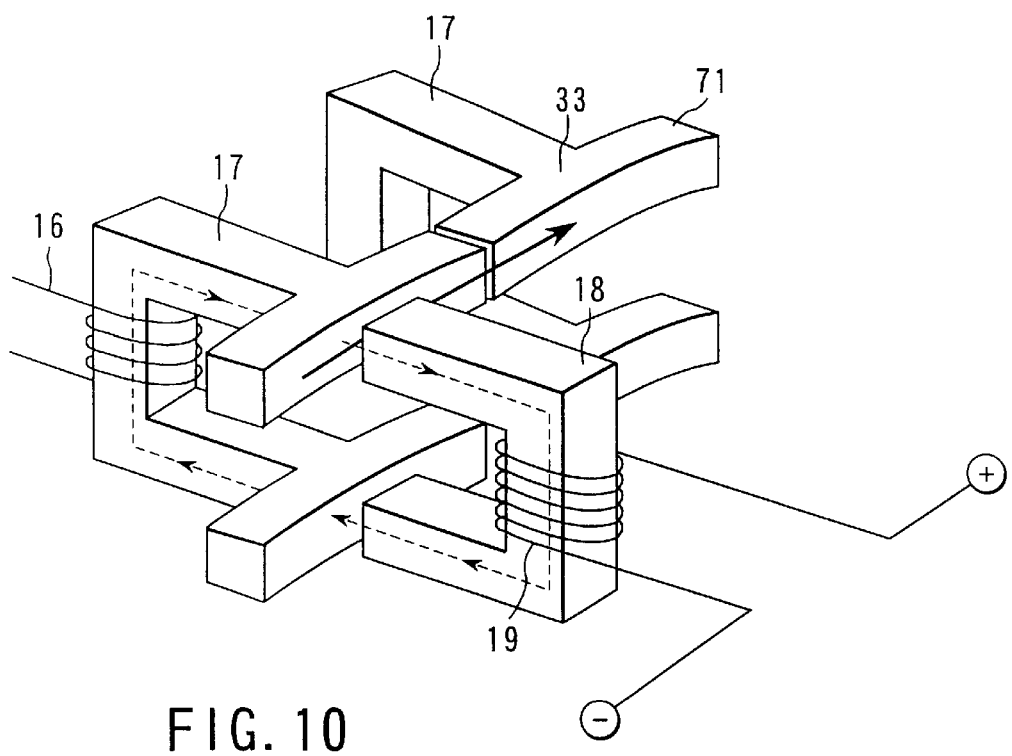
FIG. 10 is a perspective view showing the arrangement of the primary side core and secondary side core in a separate-type high-voltage transformer.

FIG. 8 shows a detailed configuration of the transformer rotating section on the rotatable gantry section in an X-ray CT apparatus according to the second embodiment. FIG. 9 shows the location of the transformer fixing section on the static gantry section and the transformer rotating section on the rotatable gantry section which face each other. FIG. 10 is a perspective view showing the arrangement of the primary side core and secondary side core in a separate-type high-voltage transformer.

A plurality of high-voltage unit blocks, for example, as shown in FIG. 8, four high-voltage unit blocks B1 to B4 are arranged on the gantry section 22 to form a circumference as a whole. These blocks are connected electrically to each other by connectors C1 to C4. One high-voltage unit block includes, for example, four high-voltage units 23, m1 to m4. This divided structure facilitates the replacement of the high-voltage units 23. Such a divided structure may be applied to the transformer fixing section of the static gantry section 12.

As shown in FIG. 9, the primary coil 16 and primary side core 17 on the static gantry section 12 are provided so as to face the secondary coil 19 and secondary side core 18 on the rotatable gantry section 22. The shape of and the number of the secondary side cores 18 are so determined that all of the plurality of primary side cores 17 never fail to the secondary side cores 18, even when the rotary section (rotatable gantry section 22) rotates.

The spacing between the primary side core 17 and the secondary side core 18 is about 1 mm. Note that the spacing is not limited 1 mm.

As shown in FIG. 10, the primary coil 16 is wound on the primary side core 17 whose cross section perpendicular to the direction of rotation of the rotatable gantry section 22 is shaped like an almost squared U. The primary coil 16 is wound on the central part of the squared-U shape of the primary side core 17. The primary side core 17 is so positioned that the two ends of the squared U may face the rotatable gantry section 22 and the straight line connecting the two ends be perpendicular to the direction of rotation of the rotatable gantry section 22. The direction in which the rotatable gantry section 22 rotates at that time is shown by a thick arrow.

At the ends of the squared-U shape of the primary side core 17, there are provided two projecting sections 71 of the same shape which project in the direction opposite to the direction of rotation of the rotatable gantry section 22. The projecting sections 71 may be made of the same material as that of the primary side core 17 or of a magnetic substance made of a material with different susceptibility. One projecting section 71 may be spaced, for example, about 1 mm apart from the projecting section 71 of the other primary side core 17. According to this gap of 1 mm, well convertibility of the primary side cores 17 is achieved. Alternatively, they may be jointed together without any gap. In this case, the leakage flux is avoided between the integral cores 17.

As shown in FIG. 9, the secondary side core 18 is provided around the rotatable gantry section 22 so as to face the primary-side core 17. As shown in FIG. 10, like the primary side core 17, the secondary side core 18 is shaped like a squared U. On the central portion of the squared-U shape, the secondary coil 19 is wound. The secondary side core 18 is so arranged that the ends of the squared U are forced to face the static gantry section 12 and conversely the central portion of the squared U is caused to face the rotatable gantry section 22, thereby making the straight line connecting the two ends of the squared U perpendicular to the direction of rotation of the rotatable gantry section 22.

In FIG. 10, only two cores on the primary side of the high-voltage transformer and only one core on its secondary side are shown. Actually, however, many cores are present on each of the primary side and secondary side and form a circumference as a whole. The many secondary side cores rotate as the rotatable gantry section rotates. The shape, number, and arrangement of the primary and secondary side cores are so determined that the secondary side cores never fail to face the primary side cores.

In the present embodiment, the primary side core has two near-rectangular open faces and the secondary side core has two near-square open faces, when viewed from the plane across which the primary and secondary side cores face each other. Making the open faces of the secondary side core smaller than those of the primary side core enables the rotatable gantry section to be made lighter, facilitating insulation. To improve the power supply efficiency, the open faces of the secondary side core may be made larger. Furthermore, the shape of the primary side core and that of the secondary side core may be made the same not only to improve the power supply efficiency but also to facilitate the manufacture.

The magnetic flux generated by the current passed through the primary coil 16 reaches the open faces of the secondary side core 18 by way of the open faces (or the ends of the squared U) of the primary side core 17. The magnetic field generated at that time is shown by a broken-line arrow. The magnetic flux causes the secondary coil 19 wound around the secondary side core 18 to generate current, thereby supplying power from the static gantry section 12 to the rotatable gantry section 22.

With this configuration, power can be supplied continuously, with the primary coil separate from the secondary coil. It should be noted that the flux from the primary side is easily and reliably transmitted to the secondary side according to an existence of the open face (projecting section 71).

As described above, with the present invention, it is possible to provide a thin-type X-ray computer tomography apparatus with a small-sized high-voltage transformer capable of supplying power and stepping up the voltage to the high voltage which is necessary for generating X-ray at the same time by a noncontacting rotary method.

Although no shown, it goes without saying that ripples in the high-voltage output due to the unevenness of the intensity of the magnetic coupling during rotation are removed by the negative feedback of the output voltage, as are ripples resulting from other causes. The negative feedback is effected by optical transmission or by radio.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus comprising:
   a static gantry section;
   a rotatable gantry section which is provided on said static gantry section in a rotatable manner and has an X-ray tube for generating X rays;
   a frequency converting circuit which is connected to an alternating-current power source and converts the output voltage from the alternating-current power source into a desired high-frequency voltage;
   a high-voltage transformer which transmits the output of said frequency converting circuit from said static gantry section to said rotatable gantry section and steps up the output to a desired high voltage; and
   a rectifier circuit which converts the alternating-current voltage outputted from said high-voltage transformer into a direct-current voltage and supplies the direct-current voltage to said X-ray tube, wherein
   said high-voltage transformer including:
      a primary-side which is provided on said static gantry section and to which the output of said frequency converting circuit is supplied, and
      a resonance circuit with a capacitor connected to a winding of a secondary-side, which is provided on said rotatable gantry section and generates said high voltage.

2. The X-ray computer tomography apparatus according to claim 1, wherein
   said frequency converting circuit includes
      a converter which converts the output voltage from said alternating-current power source into a direct-current voltage, and
      at least one inverter which converts the direct-current voltage outputted from said converter into said high-frequency alternating-current voltage.

3. The X-ray computer tomography apparatus according to claim 1, wherein said primary-side of said high-voltage transformer is placed on a circumference of said static gantry section, and
   said secondary-side of said high-voltage transformer is placed on the circumference of said rotatable gantry section having the same center as that of said static gantry section and rotates in no contact with said primary-side, while facing said primary-side.

4. The X-ray computer tomography apparatus according to claim 1, wherein said primary-side of said high-voltage transformer is composed of a primary side core and a primary winding wound around the primary side core and connected to the output terminal of said frequency converting circuit, and
   said secondary-side of said high-voltage transformer is composed of a secondary side core and a secondary winding wound around the secondary side core and connected to the input terminal of said rectifier circuit.

5. The X-ray computer tomography apparatus according to claim 4, wherein at least one of said primary side core and said secondary side core having an open face.

6. The X-ray computer tomography apparatus according to claim 1, wherein said primary-side of said high-voltage transformer including:
   a primary-side pair which is composed of a plurality of primary side cores and a plurality of primary windings wound around the respective primary side cores, and a plurality of units of the primary-side pair being provided on the circumference on said static gantry section.

7. The X-ray computer tomography apparatus according to claim 6, wherein said primary side core is shaped like a rectangle one side of which is cut out and has open face long in the direction of said circumference.

8. The X-ray computer tomography apparatus according to claim 1, wherein the secondary-side of said high-voltage transformer including:
   a secondary-side pair which is composed of a plurality of secondary side cores and a plurality of secondary windings wound around the respective secondary side cores, and a plurality of units of the secondary-side pair being provided on the circumference on said rotatable gantry section.

9. The X-ray computer tomography apparatus according to claim 8, wherein said secondary side core is shaped like a rectangle one side of which is cut out and has open face long in the direction of said circumference.

10. An X-ray computer tomography apparatus comprising:
    a static gantry section;
    a rotatable gantry section which has an X-ray tube for radiating X rays and is rotatable with respect to said static gantry section; and
    power transmission section which transmits power from said static gantry section to said rotatable gantry section in a noncontacting manner, wherein said power transmission section includes a high-voltage transformer that steps up said power and has such a divided structure as has its primary side on said static gantry section and its secondary side on said rotatable gantry section.

11. An X-ray computer tomography apparatus comprising:

a static gantry section;

a rotatable gantry section which has an X-ray tube for radiating X rays and is rotatable with respect to said static gantry section; and power transmission section which transmits power from said static gantry section to said rotatable gantry section in a noncontacting manner, wherein said rotatable gantry section does not have the primary side of said high-voltage transformer for stepping up power.

12. The X-ray computer tomography apparatus according to claim 10, wherein the secondary side of said high-voltage transformer rotates with respect to the primary side of said high-voltage transformer as said rotatable gantry section rotates.

13. The X-ray computer tomography apparatus according to claim 10, wherein said static gantry section includes a power source, a converter for converting the voltage from the power source into a direct-current voltage, and one or more inverters for converting said direct-current voltage into an alternating-current voltage, and said rotatable gantry section includes a rectifier for rectifying the output voltage stepped up by said high-voltage transformer into a direct-current high voltage and outputting the direct-current high voltage to said X-ray tube.

14. The X-ray computer tomography apparatus according to claim 10, wherein the primary side of said high-voltage transformer is composed of a plurality of primary-coil-wound primary side cores arranged so as to form a circumference as a whole, and the secondary side of said high-voltage transformer is provided with secondary-coil-wound secondary side cores arranged so as to face said primary side cores.

15. The X-ray computer tomography apparatus according to claim 14, wherein the secondary side of said high-voltage transformer further includes a resonance circuit that resonates with the inductance of said secondary coils.

16. The X-ray computer tomography apparatus according to claim 14, wherein the shape of and the number of said secondary side cores are so determined that all of said plurality of primary side cores never fail to said secondary side cores, even when said rotary section rotates.

17. The X-ray computer tomography apparatus according to claim 14, wherein said plurality of primary sides of said high-voltage transformer are connected in parallel via said inverters, and said plurality of secondary sides of said high-voltage transformer are connected in series via said rectifier.

18. The X-ray computer tomography apparatus according to claim 14, wherein said secondary-coil-wound secondary side cores are evenly arranged on the secondary side of said high-voltage transformer.

19. The X-ray computer tomography apparatus according to claim 15, wherein the primary side of said high-voltage transformer further includes another resonance circuit that resonates with the inductance of said primary coils.

20. An X-ray computer tomography apparatus comprising:

a static gantry section having an imaging volume;

a rotatable gantry section mounted opposed to the static gantry section, which rotates around the imaging volume;

an alternating-current power source provided in the static gantry section;

a plurality of primary coils which are arranged around the imaging volume of the static gantry section and electrically connected to the alternating-current power source;

a plurality of primary side cores to each of which the respective primary coils is wound;

a plurality of secondary side cores arranged on the rotatable gantry section so as to oppose to the primary cores;

a plurality of secondary cores which are wound around the respective secondary side cores;

a plurality of resonance circuits one of which is connected to each one of the secondary cores;

a rectifier circuit which rectifies the outputs of the resonance circuits; and an X-ray tube connected to the rectifier circuit.

* * * * *